United States Patent [19]

Nakanishi et al.

[11] Patent Number: 5,290,694
[45] Date of Patent: Mar. 1, 1994

[54] RECOMBINANT DNA, BACTERIUM OF THE GENUS PSEUDOMONAS CONTAINING IT, AND PROCESS FOR PREPARING LIPASE BY USING IT

[75] Inventors: Yuji Nakanishi; Yoshiaki Kurono; Yoshinao Koide, all of Aichi; Teruhiko Beppu, Tokyo, all of Japan

[73] Assignee: Amano Pharmaceutical Co., Ltd., Aichi, Japan

[21] Appl. No.: 317,827

[22] Filed: Feb. 28, 1989

[30] Foreign Application Priority Data

Feb. 28, 1988 [JP] Japan ................... 63-045557
Nov. 28, 1988 [JP] Japan ................... 63-300386

[51] Int. Cl.$^5$ .............. C12N 15/31; C12N 15/55; C12N 15/78; C12N 15/67
[52] U.S. Cl. .................. 435/198; 435/69.1; 435/172.2; 435/252.34; 435/320.1; 536/23.2; 536/23.7; 935/9; 935/14; 935/27; 935/49; 935/72
[58] Field of Search ............ 435/69.12, 172.3, 320, 435/252.3, 69.1, 320.1, 252.34; 536/27, 23.2

[56] References Cited

FOREIGN PATENT DOCUMENTS 0204284 9/1989 European Pat. Off. .
9100908 1/1991 PCT Int'l Appl. ............. 435/69.1

OTHER PUBLICATIONS

Kugimiya, W. et al., 1986, Biochemical and Biophysical Research Communications 14(1): 185-190.
Lonon, M. K., et al., 1987, Abstracts of the Annual Meeting of the American Society for Microbiology, Mar. 1-6, 1987, #K-135, p. 225.
Tsygankov, T. D. and A. Y. Chistoserdov, 1985, Plasmid 14: 118-125.
Liebl, W. and F. Götz, 1986, Molecular and General Genetics 204:166-173.
Fiedler, S. and R. Wirth, 1988, Analytical Biochemistry 170: 38-44.
Joergensen, S., et al., 1991, Journal of Bacteriology 173(2): 559-567.
Journal of General Microbiology, vol. 134, 1988, pp. 433-440; S. Wohlfarth et al., "Chromosomal Mapping and Cloning of the Lipase Gene of *Pseudomonas aeruginosa*".
Curr. Top. Microbiol. Immunol, vol. 96, 1982, pp. 47-67; M. Bagdasarian et al., "Host Vector Systems for Gene Cloning in Pseudomonas".
Ihara, F., et al., 1992, Journal of Fermentation and Bioengineering, 73(5): 337-342.
Iizumi, T., et al., 1991, Agricultural and Biological Chemistry, 55(a): 2349-2357.
Gilman, J. P., 1953, Journal of Bacteriology, 43(2):48-52.
Buchanan, R. E. and Gibbons, N. E. Editors, Bergey's Manual of Determinative Microbiology, Eighth Edition, 1974, p. 357.

Primary Examiner—Robert A. Wax
Assistant Examiner—William W. Moore
Attorney, Agent, or Firm—Wegner, Cantor, Mueller & Player

[57] ABSTRACT

A recombinant DNA capable of being replicated in a bacterium of the genus Pseudomonas is disclosed. The DNA contains a wide host range plasmid vector having a gene that codes for lipase. A process for producing lipase by transforming a host bacterium with the recombinant DNA is also described.

17 Claims, 4 Drawing Sheets

```
                10                                         20
MetAlaArgSerMetArgSerArgValValAlaGlyAlaValAlaCysAlaMetSerVal 30                                         40
AlaProPheAlaGlyMetThrAlaAlaMetThrLeuAlaThrThrArgAlaAlaMetAla 50                                         60
AlaSerAlaProAlaAspAsnTyrAlaAlaThrArgTyrProIleIleLeuValHisGly 70                                         80
LeuThrGlyThrAspLysTyrAlaGlyValLeuGluTyrTrpTyrGlyIleGlnGluAsp 90                                        100
LeuGlnGlnArgGlyAlaTheValTyrValAlaAsnLeuSerGlyPheGlnSerAspAsp 110                                        120
GlyProAsnGlyArgGlyGluGlnLeuLeuAlaTyrValLysThrValLeuAlaAlaThr 130                                        140
GlyAlaThrLysValAsnLeuValGlyHisSerGlnGlyGlyLeuThrSerArgTyrVal 150                                        160
AlaAlaValAlaProAspLeuValAlaSerValThrThrIleGlyThrProHisArgGly 170                                        180
SerGluPheAlaAspPheValGlnGlyValLeuAlaTyrAspProThrGlyLeuSerSer 190                                        200
ThrValIleAlaAlaPheValAsnValPheGlyIleLeuThrSerSerSerAsnAsnThr 210                                        220
AsnGlnAspAlaLeuAlaAlaLeuLysThrLeuThrThrAlaGlnAlaAlaThrTyrAsn 230                                        240
GlnAsnTyrProSerAlaGlyLeuGlyAlaProGlySerCysGlnThrGlyAlaProThr 250                                        260
GluThrValGlyGlyAsnThrHisLeuLeuTyrSerTrpAlaGlyThrAlaIleGlnPro 270                                        280
ThrIleSerValPheGlyValThrGlyAlaThrAspThrSerThrIleProLeuValAsp 290                                        300
ProAlaAsnAlaLeuAspProSerThrLeuAlaLeuPheGlyThrGlyThrValMetVal 310                                        320
AsnArgGlySerGlyGlnAsnAspGlyValValSerLysCysSerAlaLeuTyrGlyGln 330                                        340
ValLeuSerThrSerTyrLysTrpAsnHisLeuAspGluIleAsnGlnLeuLeuGlyVal 350                                        360
ArgGlyAlaAsnAlaGluAspProValAlaValIleArgThrHisAlaAsnArgLeuLys

LeuAlaGlyVal
```

FIG. 3B

```
                10                                          20
MetAlaSerArgAspGlyHisGlyArgArgValAlaGlyArgGlySerAlaGlyGlyAla
                30                                          40
AlaAlaAlaProProGlnAlaAlaLeuProAlaSerThrGlyLeuProSerSerLeuAla
                50                                          60
GlySerSerAlaProArgLeuProLeuAspAlaGlyGlyHisLeuAlaLysSerArgAla
                70                                          80
ValArgAspPhePheAspTyrCysLeuThrAlaGlnSerAspLeuSerAlaAlaAlaLeu
                90                                         100
AspAlaPheValValArgGlnIleAlaAlaGlnLeuAspGlyThrValAlaGlnAlaGlu
               110                                         120
AlaLeuAspValTrpHisArgTyrArgAlaTyrLeuAspAlaLeuAlaLysLeuArgAsp
               130                                         140
AlaGlyAlaValAspLysSerAspLeuGlyAlaLeuGlnLeuAlaLeuAspGlnArgAla
               150                                         160
SerIleAlaTyrArgThrLeuGlyAspTrpSerGlnProPhePheGlyAlaGluGlnTrp
               170                                         180
ArgGlnArgTyrAspLeuAlaArgLeuLysIleAlaGlnAspArgThrLeuThrAspAla
               190                                         200
GlnLysAlaGlnArgLeuAlaAlaLeuGluGlnGlnMetProAlaAspGluArgAlaAla
               210                                         220
GlnGlnArgValAspGlnGlnArgAlaAlaIleAspArgIleAlaGlnLeuGlnLysSer
               230                                         240
GlyAlaThrProAspAlaMetArgAlaGlnLeuThrGlnThrLeuGlyProGluAlaAla
               250                                         260
AlaArgValAlaGlnMetGlnGlnAspAspAlaSerTrpGlnSerAlaThrArgThrMet
               270                                         280
ArgArgSerValArgArgSerSerArgProAlaCysArgArgArgIleAlaThrProArg
               290                                         300
SerProHisCysGlySerAlaArgSerArgAsnProAlaLysArgCysGlyArgHisArg
               310
SerIleAlaAlaArgGlySerAlaAlaValThrArgAlaAlaArgCysAla
```

RECOMBINANT DNA, BACTERIUM OF THE GENUS PSEUDOMONAS CONTAINING IT, AND PROCESS FOR PREPARING LIPASE BY USING IT

BACKGROUND OF THE INVENTION

1. Field of the Invention

The present invention relates to a recombinant DNA, a bacterium of the genus Pseudomonas containing it, and a process for preparing lipase by using it.

Lipase is an enzyme capable of hydrolyzing a lipid, and utilized in an extensive field such as application in fats and oils processing, diagnostic reagents, detergents, etc.

2. Related Background Art

Hitherto, there are reports on the preparation of the lipase producing bacteria of the genus Pseudomonas by utilization of recombinant DNA techniques (Ohtera et al's Japanese Patent Laid-Open No. 60-188072, Kugimiya et al's Japanese Patent Laid-Open No. 62-228279).

These, however, are techniques in which the lipase is produced using *Escherichia coli* as a host.

As well known, in the instance where *Escherichia coli* is used as a host, products are accumulated in bacterial cells, and little secreted into culture mediums, so that the *Escherichia coli* must be crushed by ultrasonic treatment etc. followed by collection of the products, bringing about disadvantages in the production of the substances such as enzymes.

SUMMARY OF THE INVENTION

Now, the present inventors considered that it may be possible to accumulate lipase in a large quantity in the culture medium if restriction endonuclease cleavage fragments containing lipase genes, and plasmids are used, and also transformants comprised of bacteria of the genus Pseudomonas as a host are obtained, and they made intensive studies to accomplish the present invention.

The present invention provides a recombinant DNA, a bacterium of the genus Pseudomonas containing it, and a process for preparing lipase by using it, which process comprises separating a restriction endonuclease cleavage fragment originating from the bacterium of the genus Pseudomonas and containing a lipase gene to obtain plasmids having said restriction endonuclease cleavage fragment, inserting DNA into the bacterium of the genus Pseudomonas by use of these plasmids to obtain a transformant, culturing said transformant to accumulate lipase outside the bacterial cell in a large quantity, and collecting the secreted lipase.

According to one aspect of the present invention, there is provided a novel recombinant DNA, capable of being replicated in a bacterium of the genus Pseudomonas, wherein the DNA comprises a wide host range plasmid vector into which a gene that codes for lipase has been inserted.

According to another aspect of the present invention, there is provided a novel bacterium of the genus Pseudomonas inserted with a novel recombinant DNA, wherein the DNA comprises a vector into which DNA that originates from a bacterium of the genus Pseudomonas and carries genetic information for lipase has been inserted.

According to still another aspect of the present invention, there is provided a novel DNA, wherein the DNA that originates from a bacterium of the genus Pseudomonas and carries genetic information for lipase comprises a structural gene of lipase and a gene participating in the production of lipase.

Figure 3B:
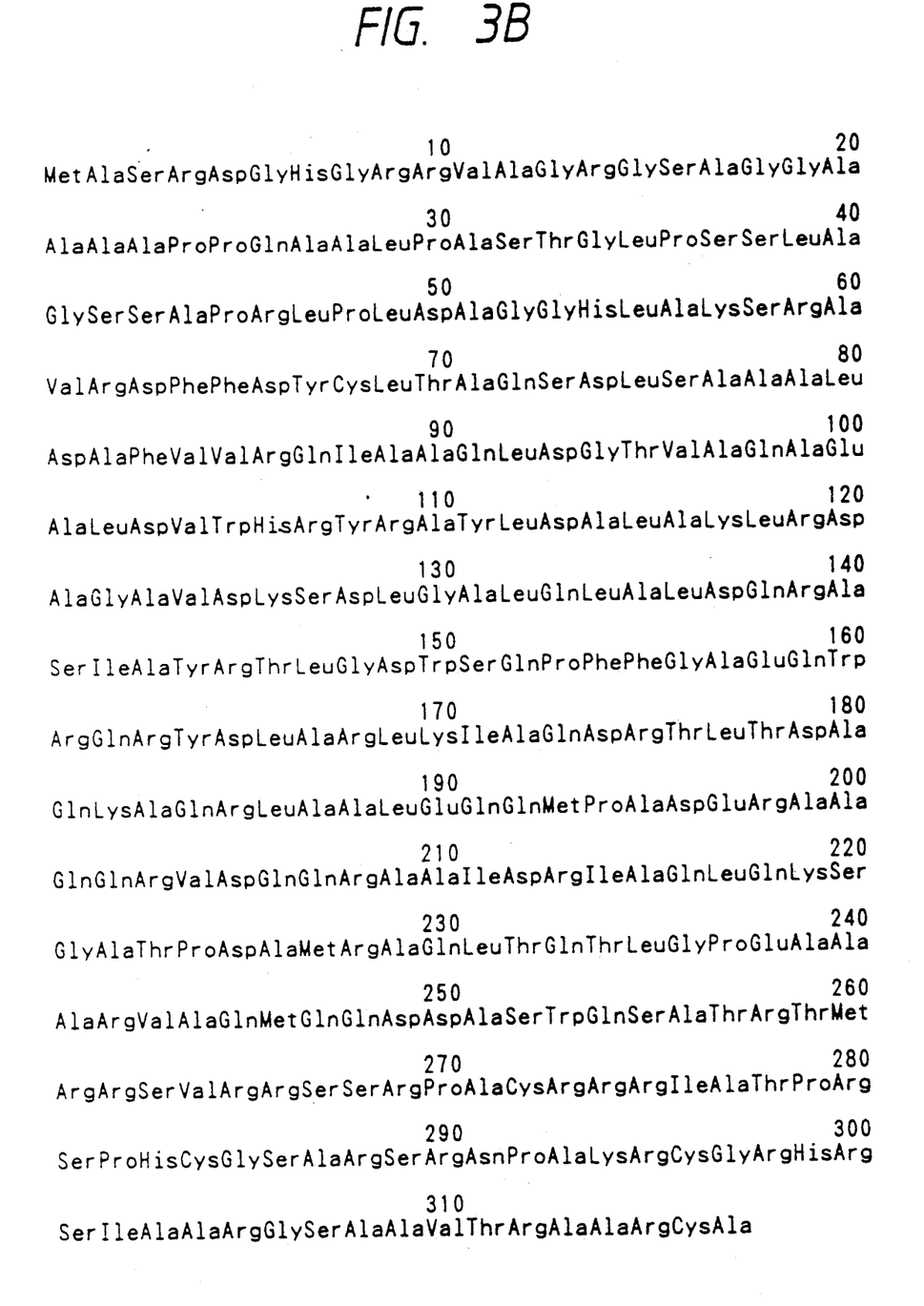

According to a further aspect of the present invention, there is provided a novel DNA, wherein a structural gene of lipase and a gene participating in the production of lipase encode the amino acid sequences as shown in FIGS. 3A and 3B, respectively.

According to an additional aspect of the present invention, there is provided a process for producing lipase, comprising:

inserting a novel recombinant DNA into a host bacterium, wherein the DNA comprises a vector into which DNA that originates from and carries genetic information for lipase has been inserted;

culturing said bacterium to cause the lipase to be produced in a cultured product; and collecting the lipase from said cultured product.

BRIEF DESCRIPTION OF THE DRAWINGS

FIG. 2 also shows fragments having lipase activity from transformed *Pseudomonas cepacia* HW10 identified on the basis of halo formation in a triolein culture medium.

FIGS. 3A and 3B each show the amino acid sequence of the DNA that carries the genetic information of lipase of *Pseudomonas cepacia*, in which FIG. 3A shows a structural gene of lipase and FIG. 3B shows an amino acid sequence of the DNA that participates in the occurrence of lipase. The underlined portion in FIG. 3A indicates the region at which the N-terminal amino acid sequence of a purified lipase protein has been determined.

DETAILED DESCRIPTION OF THE PREFERRED EMBODIMENTS

A source of the chromosomal DNA containing the lipase gene of the present invention is supplied from bacteria of the genus Pseudomonas having the ability to produce lipase. For example, it includes the strain named Pseudomonas sp. M-12-33 isolated by Arima et al [Agr. Biol. Chem., 30, 515 (1966)]. This strain has the following bacteriological properties.

(a) Morphology:
    (1) Rods (0.5 to 1.0 × 1.2 to 3.0μ).
    (2) Singly or short chains
    (3) Motile by one to three polar flagella.
    (4) No spore.
    (5) Gram stain: Negative.
    (6) Acid-fast: Negative.
    (7) Polymorphism: None.

(b) Growth state:
    (1) Nutrient agar plate culture: Circular, convex, smooth and thin on its surface, and yellowish white and transparent.
    (2) Nutrient slant culture: Filamentous, smooth on peripheries with moderate growth, convex, and pale yellowish white with slight gloss.
    (3) Nutrient liquid culture: Moderate growth, forming a thin film on the surface, and turbid.
    (4) Nutrient gelatin stab culture: Ordinary growth, and liquefied in a funnel form.
    (5) Litmus milk: Slightly alkaline, reducing litmus, and liquefied, but slightly forming a precipitate.

-continued (c) Growability:
  (1) MacConkey medium: Growth.
  (2) KCN medium: No growth.
  (3) SS agar medium: Growth.
(d) Physiological properties:
  (1) Reduction of nitrate: Positive (succinic acid, sodium nitrate medium)
  (2) Denitrification reaction: Negative.
  (3) MR test: Negative.
  (4) VP test: Negative.
  (5) Formation of indole: Negative.
  (6) Formation of hydrogen sulfide: Negative.
  (7) Hydrolysis of starch: Negative.
  (8) Utilization of citric acid: Positive (Simmon's citrate medium).
  (9) Utilization of inorganic nitrogen source:
  Nitrate is not utilized, but ammonium salt is utilized.
  (10) Formation of pigment:
    King A medium: Pale-yellow pigment.
    King B medium: Pale-brown water-soluble pigment.
    S.C.D. medium: Pale-brown pigment.
    Tyrosine medium: Slightly-brown water-soluble pigment.
    Glutamic acid agar medium: Pale-yellow water-soluble pigment.
  (11) Tween 80 decomposition: Positive.
  (12) Casein decomposition: Positive.
  (13) PHB accumulation: Positive.
  (14) Urease: Negative.
  (15) Oxidase: Positive.
  (16) Catalase: Positive.
  (17) Arginine dihydrolase: Negative.
  (18) Lysine dicarboxylase: Positive.
  (19) Ornithine dicarboxylase: Positive.
  (20) Acyl amidase: Positive.
  (21) Growth pH: 5.0 to 9.0
  (22) Growth temperature:
    10° C. (+), 20° C. (++), 25° C. (++++),
    30° C. (++++), 35° C. (++), 37° C. (−),
    42° C. (−).
  (23) Behavior to oxygen: Aerobic.
  (24) O-F test: Oxidative.
  (25) Formation of acid and gas from saccharides:
    a) Formation of acid: As shown in Table 1.
    b) Formation of gas: Negative.

TABLE 1

| Saccharides | Formation of acid |
|---|---|
| L-arabinose | + |
| D-xylose | + |
| D-glucose | + |
| D-mannose | + |
| D-fructose | + |
| Maltose | + |
| Sucrose | + |
| Lactose | + |
| Trehalose | + |
| D-sorbitol | + |
| D-mannitol | + |
| Inositol | + |
| Glycerol | + |
| Starch | − |
| D-galactose | + |

The above taxonomical properties were studied with reference to Manual of Microbiological Method (edited by American Bacteriological Society); SAIKINGAKU JISSHU TEIYOU (Manual of Bacteriology Practice); edited by The University of Tokyo, Friend Society of Infections Diseases Research Institute), etc., and comparison of these properties with what are described in Bergey's Manual of Determinative Bacteriology 8th Edition, Robert E. et al's Gramnegative Organisms: An approach to Identification (Guide to Presumptive Identification) and Cowan's Manual for the Identification of Medical Bacteria, revealed that almost all the properties except the growth temperature are coincident with those of *Pseudomonas cepacia*. Thus, the present bacterium was named *Pseudomonas cepacia* M-12-33. This strain is deposited in Fermentation Research Institute, Agency of Industrial Science and Technology, under FERM BP-2293.

Preparation of transformant

The chromosomal DNA and transformant according to the present invention can be prepared by the following procedures.

(1) Procedure for the preparation of chromosomal DNA

The *Pseudomonas cepacia* M-12-33 strain (FERM BP-2293) is cultured overnight at 30° C. under aerobic conditions, using an LB medium (tryptone: 1.0%; yeast extract: 0.5%; sodium chloride: 1.0%). Bacterial cells are collected, followed by extraction and purification of the chromosomal DNA by utilizing a known method such as the saito and Miura's method [Biochem. Biophys. Acta., 72, 619–629 (1963)].

(2) Procedure for the insertion of DNA fractions into plasmid vectors and the transformation Plasmid vectors may preferably be vectors capable of being replicated in a host, having a known restriction endonuclease cleavage pattern, and having a selective marker for chemical resistance and the like. For example, they include wide host range plasmid vectors such as RSF1010, R1b679 and R1162. More specifically, there can be used pFL100 obtained by incorporating a kanamycin-resistance gene into RSF1010.

The vector DNA thus obtained is cleaved with a restriction enzyme such as EcoRI and the chromosomal DNA is cleaved with the like restriction enzyme: The DNAs are purified and joined according to a known method using ligase or the like, thus obtaining a recombinant plasmid.

Subsequently, using the recombinant plasmid, bacteria of the genus Pseudomonas as exemplified by *Pseudomonas cepacia*, *Pseudomonas putida*, etc. are subjected to transformation.

The transformation is carried out by utilizing a calcium chloride method, a rubidium chloride method, an electroporation method.

Transformed bacterium having the ability to produce lipase may be selectively separated by simply using an agar medium containing triglycerides such as tributyrin and triolein, emulsified with polyvinyl alcohol, and an antibiotic substance in a predetermined concentration.

Namely, the bacteria containing lipase genes can be selectively identified from among the transformed bacteria by isolating a strain that forms a large clearing zone in the agar medium.

From the resulting bacteria, a plasmid DNA containing the lipase gene is obtained by using a known method such as an alkali method or a boiling method.

The lipase is further produced by using bacteria of the genus Pseudomonas obtained by insertion of the thus obtained plasmid DNA according to the present invention. For example, the *Pseudomonas cepacia* M-12-33 strain having the novel recombinant plasmid is cultured by using a known medium, and the lipase can be obtained by separating it from the culture supernatant and purifying the separated one.

Method for measuring lipase activity

In a test tube with a flat bottom, 5 ml of a substrate solution emulsified by mixing 75 ml of olive oil, in 225 ml of 2% polyvinyl alcohol (PVA) solution, and 4 ml of a 0.2M McIlvaine's buffer solution (pH 7) are combined and the mixture is pre-warmed at 37° C. for 5 minutes. To this mixture, 1 ml of a specimen solution is added and thoroughly mixed with shaking, and immediately the resulting solution is left to stand at 37° C. for 30 minutes. After 30 minutes, 10 ml of an acetone/ethanol (1:1) mixed solution is added and thoroughly mixed with shaking. To this solution, 10 ml of a 0.05 N sodium hydroxide solution and 10 ml of an acetone/ethanol (1:1) mixed solution are added, followed by further addition of 2 drops of a phenolphthalein reagent to carry out titration up to pH 10.00 using 0.05 N hydrochloric acid, while blowing nitrogen gas on the surface of the solution with stirring using a stirrer. The blank determination is similarly operated using purified water in place of the specimen solution. The enzyme titer is assumed to be 1 unit when 1 micromols of a fatty acid is formed in 1 minute.

The present invention will be specifically described below by the following Example.

EXAMPLE 1

(1) Preparation of chromosomal DNA

*Pseudomonas cepacia* M-12-33 (FERM BP-2293) was cultured overnight at 30° C. under aerobic conditions with shaking in LB medium, and, after collection of bacteria, the chromosomal DNA was extracted and purified according to a DNA extraction method by the Saito and Miura's method, thus obtaining 8.4 mg of the chromosomal DNA.

(2) Insertion of restriction endonuclease cleavage fragments into plasmid vectors A wide host range plasmid vector RSF1010 (330 ng) was cleaved with a restriction enzyme PstI to extract an 8.1 Kb fragment. On the other hand, a 1.4 Kb fragment containing a kanamycin-resistance gene was prepared from 480 ng of pUC-4K (available from Pharmacia Fine Chemicals, Inc.) according to the similar operation. Both were joined with a T4 DNA ligase, thereby obtaining a plasmid vector pFL100. The pFL100 was purified from an *Escherichia coli* C600 strain according to Maniatis et al's method [Maniatis et al. Molecular Cloning, a laboratory manual, 92-94 (1981)].

The above chromosomal DNA (8.4 μg) was taken up, and, with addition of a restriction enzyme EcoRI, reacted at 37° C. for 15 minutes, to cleave the DNA in part. On the other hand, the restriction enzyme EcoRI was added to 2.5 μg of the plasmid pFL100 to carry out the reaction at 37° C. for 2 hours, thus completely cleaving the DNA. To the cleaved plasmid DNA, alkaline phosphatase was added to effect dephosphorylation. The cleaved chromosomal DNA and the vector plasmid DNA were mixed, and reacted with addition of DNA ligase to carry out the reaction to join the DNA fragments.

(3) Transformation by plasmid

In selecting and separating the lipase gene in the above culture medium containing triolein, a halo-formation defective host is advantageous. Accordingly, the *Pseudomonas cepacia*, M-12-33 strain (FERM P No. 9871) was treated with nitrosoguanidine, and a mutant strain HW10 that forms no halo was obtained using Antibiotic Medium 3 (available from Difco Co.) containing 0.2% of triolein.

The present inventors found that the electroporation method is very effective for the transformation of said strain. More specifically, said strain was cultured at 30° C. using 20 ml of LB medium until it entered the logarithmic growth phase ($OD_{660}=0.4$), and then cooled, followed by centrifugal separation at 3,500 rpm for 5 minutes. The bacterial cells were washed with 10 ml of a buffer solution (pH 7.4) comprised of 272 mM sucrose and 7 mM sodium phosphate. Centrifugal separation was again carried out, followed by suspension in 0.8 ml of the like buffer solution. The joined recombinant DNA was added, and a pulse of 6,000 V/cm$^2$ was applied, followed by addition of 5.7 ml of the LB medium to carry out culture at 30° C. for 2 hours with shaking. As a result of these procedures, transformant strains were obtained with an efficiency of $2 \times 10^6$ cfu/μg of DNA.

The recombinant DNA thus joined was subjected to the electroporation method to effect the transformation of the HW10 strain, and then the transformants were spread onto a selective medium containing 500 μg/ml of kanamycin and 0.2% of triolein. As a result, 8 halo-forming strains were obtained.

(4) Identification of transformant containing lipase gene

Figure 1:
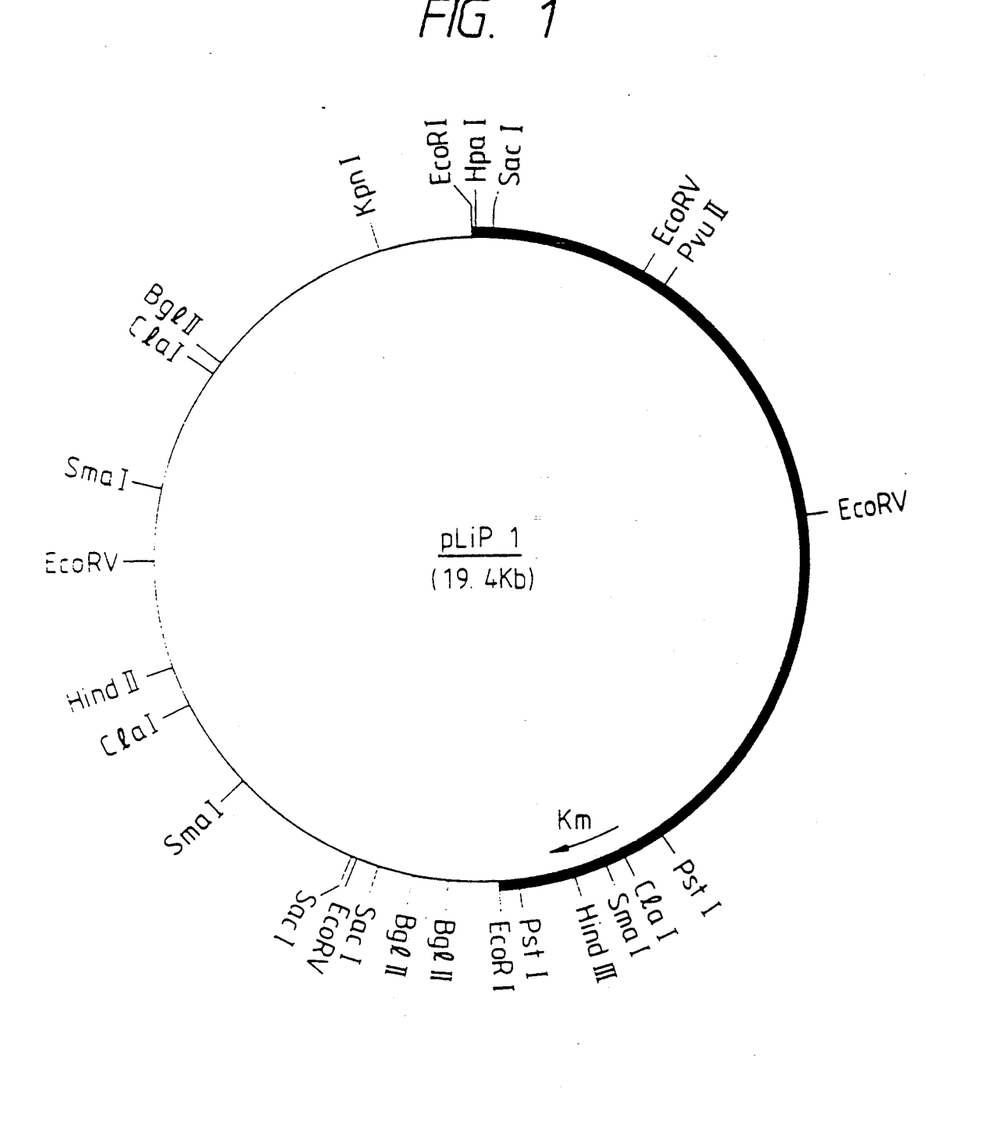
FIG. 1 shows as an example a restriction map prepared by digestion of plasmid pLiP1 by various restriction enzymes wherein the DNA fragment that codes for lipase of *Pseudomonas cepacia* M-12-33 (FERM BP-2293) is identified by agarose gel electrophoresis.

Plasmids were extracted from the above 8 halo-forming strains, and cleaved with the restriction enzyme EcoRI. The inserted restriction endonuclease cleavage fragments were analyzed by agarose electrophoresis to find that the strains were divided into those groups into which about 10 Kb of the EcoRI fragment was inserted and those containing 6.0 Kb and 2.7 Kb of EcoRI fragments. An experiment using an antilipase antiserum revealed that the desired lipase gene was present on the 10 Kb EcoRI fragment. It is considered that in fact the halo-formation defective strain HW10 did not undergo the mutation on the lipase gene, but became a halo-formation defective strain because of the mutation of other genes. Thus regarding the EcoRI fractions of 6.0 Kb and 2.7 Kb, it is considered that the transformant strain thereof formed a halo because the gene having undergone this mutation was cloned. The plasmid vector containing 10 Kb of the EcoRI fragment was named pLiP1, and its restriction enzyme cleavage map is shown in FIG. 1.

Analysis of lipase gene

Figure 2:
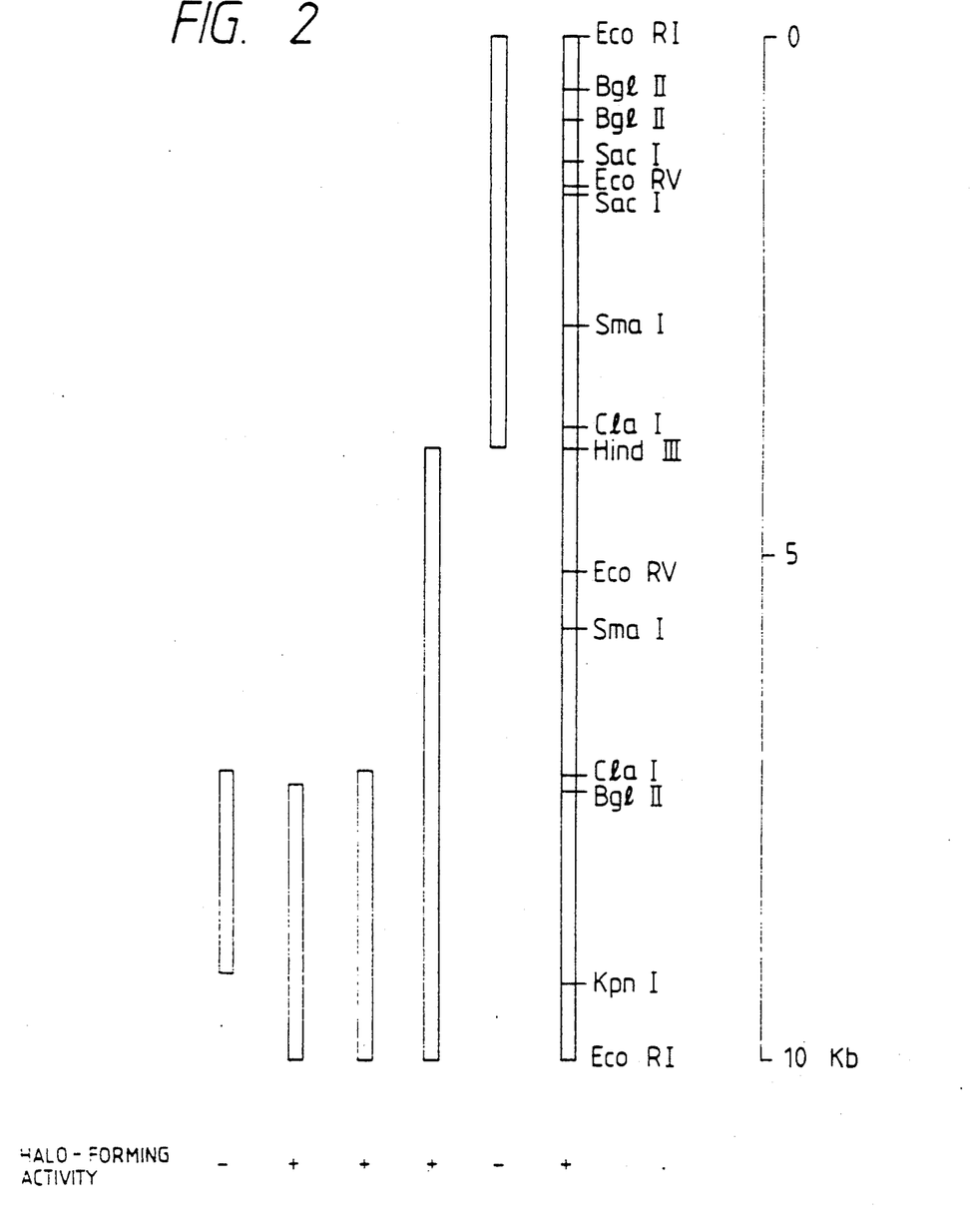
FIG. 2 shows results of the cleavage of plasmid pLiP1 with various restriction enzymes and subcloning of the DNA fractions in pFL100.

The pLiP1 plasmid was cleaved with various restriction enzymes, where each DNA fragment was subcloned to pFL100 to effect transformation of the *Pseudomonas cepacia* HW10 strain, and whether or not halo were formed in the triolein medium was examined in the same manner as the above. Results obtained are shown in FIG. 2. The plasmid pLip10 obtained by the subcloning of a 3 Kb ClaI-EcoRI also produced lipase. However, no production of lipase was observed as to the plasmid containing a 2 Kb ClaI-KpnI fragment.

The size of the main body of the lipase gene, presumably from the fact that the lipase has a molecular weight of 34,000, is considered to be about 1.1 Kb, but the result of the subcloning shows that 2 Kb or more of the restriction endonuclease cleavage fragment is required for the production of the lipase. Then, the whole base sequence of the 3 Kb ClaI-EcoRI fragment was determined according to the Mizusawa et al's method [Nucleic Acids Res., 14(3), 1319-1324 (1986)].

As a result it became clear that the 3 Kb ClaI-EcoRI fragment comprises a structural gene of lipase and a gene of the protein essential to the production of lipase. The amino acid sequence of these genes is shown in FIGS. 3A and 3B.

(5) Production of lipase

The *Pseudomonas cepacia* M-12-33 was transformed with the plasmid pLiP10 containing the above lipase gene. The present strain was cultured with shaking at 30° C. for 3 days, using a liquid medium comprising 2.0% of soybean oil, 0.5% of peptone (available from Difco Co.), 0.3% of meat extract (available from Difco Co.), 0.1% of $KH_2PO_4$, 0.02% of $MgSO_4.7\ H_2O$, 0.001% of $FeSO_4.7\ H_2O$, and one drop of Adecanol (available from Asahi Denka). A culture supernatant with a lipase activity of 600 U/ml was obtained by centrifugal separation. This productivity was about 40 times the lipase productivity of the host bacterium *Pseudomonas cepacia* M-12-33 strain.

We claim:

1. A recombinant DNA capable of being replicated in a bacterium of the genus Pseudomonas, comprising a wide host range plasmid vector containing a DNA fragment originating from the genus Pseudomonas comprising a structural gene of lipase and a gene encoding a protein participating in the production of lipase.

2. The recombinant DNA according to claim 1, wherein the plasmid vector is plasmid RSF1010 or a plasmid originating therefrom.

3. The recombinant DNA according to claim 2, wherein said plasmid originating from RSF1010 is plasmid pFL100.

4. A recombinant bacterium of the genus Pseudomonas, transformed with a recombinant DNA, wherein said DNA comprises a vector containing a DNA fragment comprising a structural gene of lipase and a gene participating in the production of lipase, said isolated DNA fragment originating from a bacterium of the genus Pseudomonas.

5. An isolated DNA fragment originating from a bacterium of the genus Pseudomonas and coding for lipase, comprising a structural gene of lipase and a gene participating in the production of lipase.

6. The isolated DNA fragment of claim 5, wherein the structural gene of lipase and a gene participating in the production of lipase encode the amino acid sequences as shown in FIGS. 3A and 3B, respectively.

7. The recombinant bacterium according to claim 4, wherein the bacterium of the genus Pseudomonas comprises *Pseudomonas cepacia* or *Pseudomonas putida*.

8. A process for producing lipase, comprising:
   transforming a host bacterium with a recombinant DNA comprising a vector containing a DNA fragment comprising a structural gene of lipase and a gene participating in the production of lipase, said isolated DNA fragment originating from a bacterium of the genus Pseudomonas;
   culturing said bacterium to cause the lipase to be produced in culture broth; and
   collecting the lipase from said culture broth.

9. The process for producing lipase according to claim 8, wherein said gene originates from *Pseudomonas cepacia* and said transformation is carried out by an electroporation method.

10. The process for producing lipase according to claim 8, wherein said host bacterium is *Pseudomonas cepacia* or *Pseudomonas putida*.

11. A process for the preparation of lipase which comprises culturing a bacterium of claim 4 whereby said lipase is expressed in the fermentation broth.

12. The process of claim 11, wherein the vector DNA comprises plasmid RSF1010 or a plasmid originating therefrom.

13. The process of claim 12, wherein said plasmid originating from RSF1010 is plasmid pFL100.

14. The process of claim 11, wherein said structural gene of lipase comprises the amino acid sequence shown in FIG. 3A, and said gene participating in the production of lipase encodes the amino acid sequences shown in FIG. 3B.

15. The process of claim 11, wherein said recombinant bacterium comprises *Pseudomonas cepacia* or *Pseudomonas putida*.

16. The process of claim 11, wherein said vector containing a DNA sequence that codes for lipase comprises plasmid pLiP1.

17. A recombinant DNA comprising plasmid pLiP1.

* * * * *

UNITED STATES PATENT AND TRADEMARK OFFICE
CERTIFICATE OF CORRECTION

PATENT NO. : 5,290,694  
DATED : March 1, 1994  
INVENTOR(S) : Yuji Nakanishi

It is certified that error appears in the above-identified patent and that said Letters Patent is hereby corrected as shown below:

Drawings,  
Sheet 4 of 4

Delete original Figure 3B and substitute therefore Figure 3B attached hereto:

Signed and Sealed this

Nineteenth Day of February, 2002

Attest:

Attesting Officer

JAMES E. ROGAN  
*Director of the United States Patent and Trademark Office*

FIG. 3B

|  |  |
|---|---|
| 10 | 20 |
| MetThrAlaArgGluGlyArgAlaProLeu | AlaArgArgAlaValValTyrGlyValVal |
| 30 | 40 |
| GlyLeuAlaAlaIleAlaGlyValAlaMet | TrpSerGlyAlaGlyTrpHisArgGlyThr |
| 50 | 60 |
| GlyThrAlaGlyGluLeuProAspAlaAla | AlaAlaGlyGlyAlaAlaAlaAlaProPro |
| 70 | 80 |
| GlnAlaAlaLeuProAlaSerThrGlyLeu | ProSerSerLeuAlaGlySerSerAlaPro |
| 90 | 100 |
| ArgLeuProLeuAspAlaGlyGlyHisLeu | AlaLysSerArgAlaValArgAspPhePhe |
| 110 | 120 |
| AspTyrCysLeuThrAlaGlnSerAspLeu | SerAlaAlaAlaLeuAspAlaPheValVal |
| 130 | 140 |
| ArgGlnIleAlaAlaGlnLeuAspGlyThr | ValAlaGlnAlaGluAlaLeuAspValTrp |
| 150 | 160 |
| HisArgTyrArgAlaTyrLeuAspAlaLeu | AlaLysLeuArgAspAlaGlyAlaValAsp |
| 170 | 18( |
| LysSerAspLeuGlyAlaLeuGlnLeuAla | LeuAspGlnArgAlaSerIleAlaTyrArg |
| 190 | 200 |
| ThrLeuGlyAspTrpSerGlnProPhePhe | GlyAlaGluGlnTrpArgGlnArgTyrAsp |
| 210 | 220 |
| LeuAlaArgLeuLysIleAlaGlnAspArg | ThrLeuThrAspAlaGlnLysAlaGluArg |
| 230 | 240 |
| LeuAlaAlaLeuGluGlnGlnMetProAla | AspGluArgAlaAlaGlnGlnArgValAsp |
| 250 | 260 |
| GlnGlnArgAlaAlaIleAspArgIleAla | GlnLeuGlnLysSerGlyAlaThrProAsp |
| 270 | 280 |
| AlaMetArgAlaGlnLeuThrGlnThrLeu | GlyProGluAlaAlaAlaArgValAlaGln |
| 290 | 300 |
| MetGlnGlnAspAspAlaSerTrpGlnSer | ArgTyrAlaAspTyrAlaThrGlnArgAla |
| 310 | 320 |
| GlnIleGluSerAlaGlyLeuSerProGln | AspArgAspAlaGlnIleAlaAlaLeuArg |
| 330 | 340 |
| GlnArgThrPheThrLysProGlyGluAla | ValArgAlaAlaSerLeuAspArgGlyAla |